(12) United States Patent
Wang

(10) Patent No.: US 7,189,420 B2
(45) Date of Patent: *Mar. 13, 2007

(54) COMPOSITION COMPRISING WENGUANGUO EXTRACTS, METHODS FOR PREPARING SAME AND USES THEREOF

(75) Inventor: Yun Wang, Dunedin (NZ)

(73) Assignee: Fountain Silver Limited, Chai Wan (HK)

( * ) Notice: Subject to any disclaimer, the term of this patent is extended or adjusted under 35 U.S.C. 154(b) by 0 days.

This patent is subject to a terminal disclaimer.

(21) Appl. No.: 10/471,384

(22) PCT Filed: Aug. 28, 2002

(86) PCT No.: PCT/IB02/04750

§ 371 (c)(1),
(2), (4) Date: Sep. 4, 2003

(87) PCT Pub. No.: WO03/017919

PCT Pub. Date: Mar. 6, 2003

(65) Prior Publication Data

US 2004/0146591 A1    Jul. 29, 2004

(51) Int. Cl.
*A61K 36/00* (2006.01)

(52) U.S. Cl. ...................................... 424/725
(58) Field of Classification Search .................. 424/725
See application file for complete search history.

(56) References Cited

U.S. PATENT DOCUMENTS 6,616,943 B2 * 9/2003 Wang .......................... 424/451

2003/0082293 A1    5/2003 Wang et al.
2003/0096030 A1    5/2003 Wang et al.

FOREIGN PATENT DOCUMENTS

| CN | 1092991 A | 10/1994 |
| CN | 1092992 A | 10/1994 |
| CN | 1349820 A | 10/2001 |
| CN | 1350001 A | 10/2001 |

OTHER PUBLICATIONS

Chen et al. Chem. Pharm. Bull., 1985, vol. 33, No. 1, pp. 127-134.*
PCT International Preliminary Examination Report, for Fountain Silver Ltd., et al., Int'l App'l No. PCT/IB02/04750, Filed on Aug. 28, 2002, Dated Jun. 3, 2003.

(Continued)

Primary Examiner—Christopher Tate
Assistant Examiner—S. B. McCormick-Ewoldt
(74) Attorney, Agent, or Firm—Law Offices of Albert Wai-Kit Chan, LLC

(57) ABSTRACT

This invention provides a composition comprising extracts from the husk of Wenguanguo and a process of producing the combined extract comprising the following steps: extracting Wenguanguo husks with an organic solvent to form an organic extract; removing the organic solvent from the extract to form aqueous extracts; and drying and sterilizing the aqueous extracts to form the combined extracts. The extracts can be used to make medicines or health foods for preventing cerebral aging, improving memory, improving cerebral functions and curing enuresis, frequent micturition, urinary incontinence, dementia, weak intelligence and Alzheimer's disease and other diseases caused by cerebral dysfunction. The combined extracts contain saponin, saccharides, proteins and others.

7 Claims, 1 Drawing Sheet

OTHER PUBLICATIONS

Figure 1:
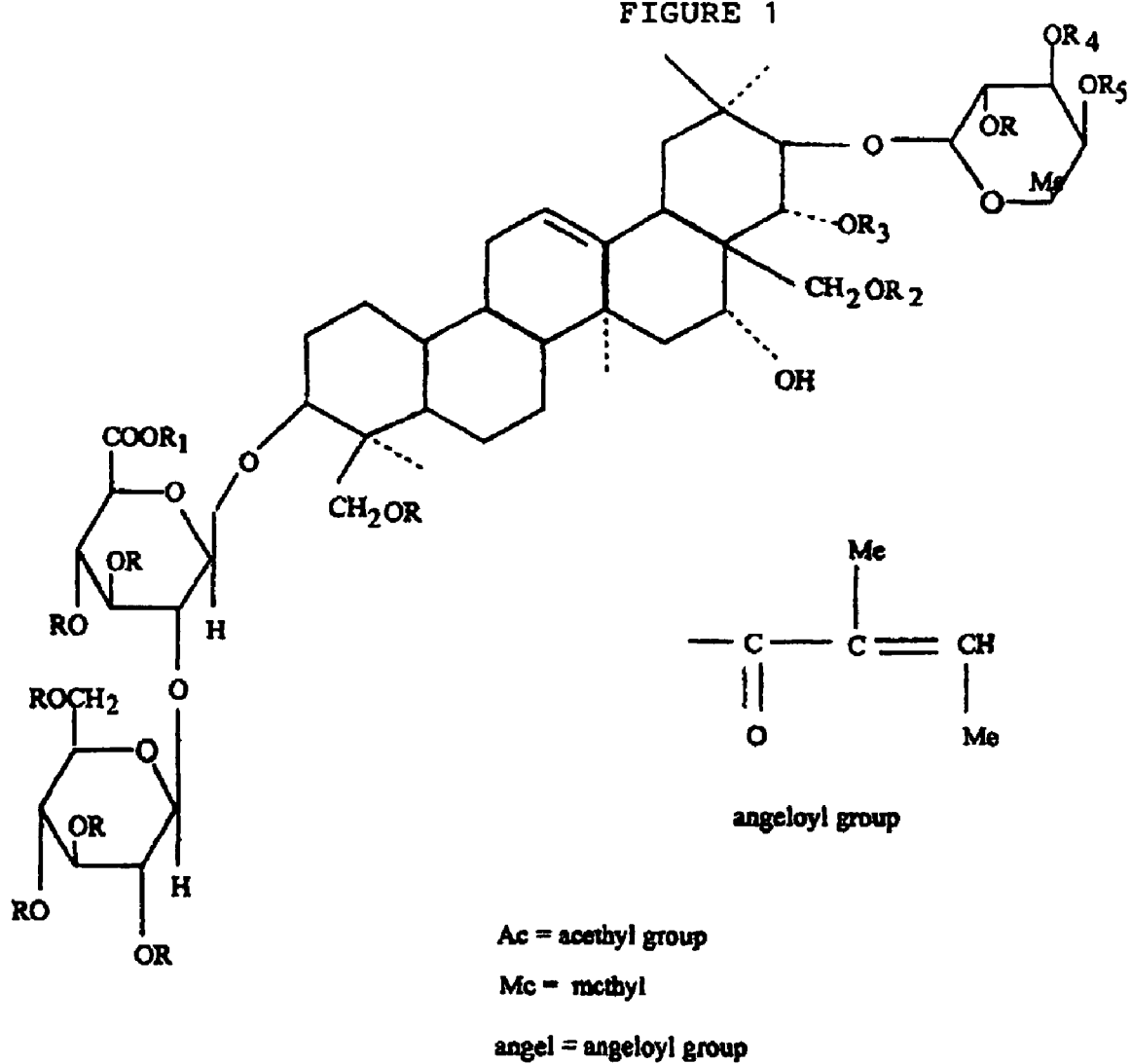

PCT International Search Report on the Declaration, for Fountain Silver Ltd., et al., Int'l App'l No. PCT/IB02/04750, Filed on Aug. 28, 2002, Dated Apr. 3, 2003.

Chen, et al. Chem. Pharm. Bull. 33(1): 127-134, 1985.

Lu Guiyuan and Wang Yitao. Study of development new Chinese medicines, 286-294, People Health Publ.

Zhang, et al. Proceedings of national conference on medicinal plants, Dalian, China, 2000.

Zhu, et al. Platae medicinals Chinae boreali-orientalis, 710-711 Heilongjiang Science & Technology Publishing House, 1989.

Y. Chen, T. Takeda and Y. Ogihara, "Studies on the Constituents of *Xanthoceras sorbifolia* BUNGE V. Major Saponins from the Fruits of *Xanthoceras sorbifolia* BUNGE1", Chem. Pharm.

Supplementary European Search Report issued on Jul. 6, 2005 for Fountain Silver Limited et al., EPO Application No. 02781502.6.

Cheng et al., "Two New Sterols in Husk of *Xanthoceras sorbifolia*", retrieved from DATABASE CA Online! Chemical Abstracts Service, Columbus, Ohio, Jun. 13, 2001, Abstract only.

Zhang et al., "Studies on Chemical Constituents of *Xanthoceras sorbifolla* Bunge", retrieved from DATABASE CA Online! Chemical Abstracts Service, Columbus, Ohio, Apr. 12, 2000, Abstract only.

Ma et al., "Inhibitory Effects on HIV-1 Protease of Constituents from the Wood of *Xantheceras sorbifolia* ", Journal of Natural Products, vol. 63, pp. 238-242, (2000).

Ma, et al. Inhibitory Effects on HIV 1 Protease of Constituents from the Wood of *Xantheoceras sorbifolia*, Journal of Natural Products (2000), vol. 63, pp. 238-242.

Cheng, et al. Two New Sterols in Husk of *Xanthoceras sorbifolia*, Chemical Abstracts Service, Database CA, Zhong Cao Yao (2001), 32(3), 199-201.

European Patent Office Communication Pursuant to Article 96(2) EPC, dated Oct. 12, 2005, for Fountain Silver Limited for European Patent Application No. 02781 502.6, filed Feb. 25, 2004.

* cited by examiner

Ac = acethyl group
Mc = methyl
angel = angeloyl group

| R | $R_1$ | $R_2$ | $R_3$ | $R_4$ | $R_5$ | |
|---|---|---|---|---|---|---|
| H | H | H | Ac | angel | Ac | A |
| H | H | H | Ac | angel | angel | B |
| H | H | Ac | H | angel | Ac | C |
| H | H | Ac | H | angel | angel | D |

Saponin Structure A, B, C, D

COMPOSITION COMPRISING WENGUANGUO EXTRACTS, METHODS FOR PREPARING SAME AND USES THEREOF

The application disclosed herein corresponds to International Application No. PCT/IB02/04750, filed Aug. 28, 2002, which claims benefit of U.S. Ser. No. 09/944,805, filed Aug. 31, 2001, the contents of which are hereby incorporated by reference into this application.

Throughout this application, various references are referred to. Disclosures of these publications in their entireties are hereby incorporated by reference into this application to more fully describe the state of the art to which this invention pertains.

FIELD OF THE INVENTION

This invention relates to combined extracts and a crude saponin extract from a plant called Wenguanguo and methods of their preparation. The extracts can be used to make medicines or health foods for preventing cerebral aging, improving cerebral functions and curing enuresis, frequent micturition, urinary incontinence, dementia, weak intelligence and Alzheimer's disease, autism, brain trauma, Parkinson's disease other diseases caused by cerebral dysfunctions, and treating arthritis, rheumatism, poor circulation, arteriosclerosis, Raynaud's syndrome.

BACKGROUND OF THE INVENTION

In recent years there has been a growing interest in finding novel extracts from plants to make medicines or health foods for preventing and curing diseases or improving human health. Using medicinal herbal plants for treating diseases or improving human health has long been a tradition in China. The Chinese herbal plants have been excellent resources for developing these extracts. More and more novel plant extracts have been developed from Chinese medicinal plants, such as Ginseng, Ginkgo, Chongcao and etc. (Zhang TCH et al., 2000).

Wenguanguo is a plant that is endemic to China (Zhu YCH et al, 1989), and it has been used as a folk remedy for curing enuresis for a long time (Chen Y et al., 1985; Zhu YCH et al, 1989). However, Wenguanguo has not been fully explored as a potential medicine or health food for preventing cerebral dysfunction and improving cerebral function. In Chinese patents CN1092991A and CN1092992A, a kernel powder made from Wenguanguo seed kernel has been studied and a medicine called Yiniaoting has been developed for the treatment of enuresis. However, the content of the bioactive ingredients Saponin in Yiniaoting is very low and therefore, large dosages are inevitable for effective treatment. Furthermore, the process of making Yiniaoting from Wenguanguo seeds is arduous, costly and complicated. In this invention two novel extracts from the Wenguanguo husks are provided and methods of producing them are developed. These extracts offer improved medicinal effects and lower processing costs.

SUMMARY OF THE INVENTION

This invention relates to combined extracts and a crude saponin extract from Wenguanguo husks and methods of their preparation. Both husk extracts have a higher saponin concentration (30–32% or more) compared with the kernel powder (2–4%) and its extracts (10–19%) in previous work. Therefore, the dosage of medicines made from the husk extracts is only 3 capsules or pills per day, compared with kernel powder, which is 18 per day. It is much easier for patients to take, children in particular, and it also greatly reduces patients' costs.

This invention provides a process of producing the two husk extracts. The cost of producing the two extracts from the husks is much lower due to the much lower cost of purchasing husks and simplified methods.

This invention provides a composition comprising extracts from the husk of Wenguanguo.

The invention also provides a process of producing the combined extract comprises following steps: a) extracting Wenguanguo husks with an organic solvent to form an organic extract; b) removing the organic solvent from the extract to form aqueous extracts; and c) drying and sterilizing the aqueous extracts to form the combined extracts.

This invention provides a crude saponin extract from Wenguanguo husks for preventing cerebral aging, improving cerebral functions and curing enuresis, frequent micturition, urinary incontinence, dementia, weak intelligence and Alzheimer's disease, autism, brain trauma, Parkinson's disease and other diseases caused by cerebral dysfunctions and treating arthritis, rheumatism, poor circulation, arteriosclerosis, Raynaud's syndrome.

This invention also provides a process of production of crude saponin extract from Wenguanguo husks comprising the steps of:
 a) extracting the wenguanguo husks by alcohol or other organic solvent at ratio of 1:2, 4–5 times, 20–35 hours each time to form alcohol extracts;
 b) collecting and refluxing the alcohol extracts 2–3 times at about 80° C. to form second extracts;
 c) collecting the second extracts and removing said solvent from the extracts to form a combined extract;
 d) resolving the combined extracts in water to from an aqueous solution;
 e) extracting the solution by n-butanol to form n-butanol extracts;
 f) chromatographing the n-butanol extracts to form crude saponin.

DETAILED DESCRIPTION OF THE FIGURES

FIG. 1. Structure of Saponin

DETAILED DESCRIPTION OF THE INVENTION

This invention provides a composition comprising extracts from the husks of Wenguanguo. This composition may be used for preventing cerebral aging, improving memory, improving cerebral functions and curing enuresis, frequent micturition, urinary incontinence, dementia, weak intelligence and Alzheimer's disease, autism, brain trauma, Parkinson's disease and other diseases caused by cerebral dysfunctions and treating arthritis, rheumatism, poor circulation, arteriosclerosis, Raynaud's syndrome.

This invention also provides a process of producing the combined extracts comprising the following steps: a) extracting Wenguanguo husks with an organic solvent to form an organic extract; b) removing the organic solvent from the extract to form aqueous extracts; and c) drying and sterilizing said aqueous extracts to form the combined extracts. In an embodiment, the solvent is alcohol, light petroleum or ether. In a further embodiment, the solvent is ethanol or methanol. In a separate embodiment, the process comprises milling, or grinding prior to the extraction step. In another embodiment, the process comprises drying the wenguanguo husks prior to the milling step. In yet another embodiment, the process comprises selecting and cleaning the Wenguanguo husks prior to the drying step.

In a further embodiment, the process comprises harvesting the Wenguanguo husks prior to the cleaning and selecting step. In an embodiment, the Wenguanguo fruits are harvested from August to October from Wenguanguo trees. In a separate embodiment, the ratio of Wenguanguo husks to alcohol is 1:2. In a further embodiment, the process comprises carrying out the extraction step 4–5 times at room temperature. In an embodiment, the extraction step is carried out 20–35 hours each time. In a different embodiment, the alcohol extracts are collected and combined.

In another embodiment, the combined extracts are refluxed at 80° C., 2–3 times. In a separate embodiment, the process comprises producing medicines or health foods from the combined extracts for treating enuresis and other diseases caused by cerebral dysfunctions and for improving cerebral functions.

This invention provides the medicines or health foods produced above. In an embodiment, the medicines or health foods are in capsule, pill, powder, liquid, injection, and other forms.

This invention also provides a compound for treating enuresis or other cerebral dysfunctions or improving cerebral functions, isolated from the combined extracts above. This invention provides the combined extracts from the above process.

This invention furthermore provides the above composition for preventing cerebral aging, improving memory, improving cerebral functions and curing enuresis, frequent micturition, urinary incontinence, dementia, weak intelligence and Alzheimer's disease, autism, brain trauma, Parkinson's disease and other diseases caused by cerebral dysfunctions, and treating arthritis, rheumatism, poor circulation, arteriosclerosis, Raynaud's syndrome.

This invention also provides the composition comprising combined extracts produced by the above process wherein the extracts are combined extracts from Wenguanguo husks, including stems of fruits. In an embodiment, said extracts from Wenguanguo are alcohol extracts. In another embodiment, said alcohol is ethanol, methanol and other organic solvents such as light petroleum or ether. In another embodiment, said combined extracts contain saponins and other compounds.

This invention also provides the above composition comprising saponin at a range of about 30–32%, saccharides at a range of about 15–25%, protein at a range of about 8–14%, water at a range of about 7–10%, and fat at a range of about 1–4%. In an embodiment, the composition comprises about 1–20% saponin. In another embodiment, the composition comprises about 10–30% saponin. In a further embodiment, the composition comprises at least 30% saponin.

This invention also provides a crude saponin extract from wenguanguo husks for preventing cerebral aging, improving cerebral functions and curing enuresis, frequent micturition, urinary incontinence, dementia, weak intelligence and Alzheimer's disease, autism, brain trauma, Parkinson's disease and other diseases caused by cerebral dysfunctions and treating arthritis, rheumatism, poor circulation, arteriosclerosis, Raynaud's syndrome. In an embodiment, the composition comprises at least 50% saponin. In a separate embodiment, the composition comprises at least 75% saponin. In another embodiment, the composition comprises at least 95% saponin.

This invention furthermore provides a process of producing the extract above comprising the steps of: a) extracting the Wenguanguo husks by alcohol or other organic solvent at a ratio of 1:2, 4–5 times, 20–35 hours each time, to form alcohol extracts; b) collecting and refluxing said alcohol extracts 2–3 times at about 80° C. to form the second extract; c) collecting the second extracts and removing the solvent from the extracts to form a combined extract; d) resolving the combined extracts in water to form an aqueous solution; e) extracting the solution by n-butanol to form n-butanol extracts; f) chromatographing the n-butanol extracts to form the crude saponin.

This invention also provides the above process comprising producing medicines or health foods from said crude saponin for treating enuresis and other diseases caused by cerebral dysfunctions and improving cerebral functions. This invention furthermore provides the medicines or health foods produced above. In an embodiment, the medicines or health foods are in capsule, pill, powder, liquid, injection, and other forms.

Finally, this invention provides the medicines or health food above further comprising Vitamin B, Vitamin D, Vitamin K, grape seed extract and other antioxidants, *Cordyceps*, or its extract, *gingko*, or its extract, *Panax ginseng* and *P. quinquefolium* or their extracts, Huangpi (*Clausena lansium*), or its extracts, *Echinacea* or its extract, St John's Wort (*Hypericum perforatum*), or its extract, Gegen (*Pueraria lobata*), or its extract, Tianma (*Gastrodia elata*), *Armillariella mellea*, or its extract, Danshen (*Salvia miltiorrhiza*), or its extract, Sanqi (*Panax notoginsen*), or its extract, Monascus or Hongu (Red yeast rice), Huangi (*Hedysarum polybotrys*), or its extract, Dihuang (*Rehmannia glutinosa*), or its extract, Danggui (*Angelica sinensis*), Yuanzhi (*Polygala tenuifoila*), or its extract, Lingzhi (*Ganoderma* spp.), or its extracts, Fuling (*Poria cocos*), or its extract, Gan Cao (*Glycyrrhiza uralensis Fisch*)or its extract, Huperzine A, Lacithin, Metrifonate, Nocetile, folic acid, amino acids, creatine, fiber supplement, or any combination thereof.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Medicines or health foods are produced from said crude saponin for treating enuresis and other diseases caused by cerebral dysfunctions and improving cerebral functions. Said medicines or health foods are made in capsule, pill, powder, liquid and other forms. The medicines or health foods further comprise Vitamin B, Vitamin D, K, an grape seed extract and other antioxidants, *Cordyceps*, or its extract, *gingko*, or its extract, *Panax ginseng* and *P. quinquefolium* or their extracts, Huangpi (*Clausena lansium*), or its extracts, *Echinacea* or its extract, St John's Wort (*Hypericum perforatum*), or its extract, Gegen (*Pueraria lobata*), or its extract, Tianma (*Gastrodia elata*), *Armillariella mellea*, or its extract, Danshen (*Salvia miltiorrhiza*), or its extract, Sanqi (*Panax notoginsen*), or its extract, Monascus or Hongu (Red yeast rice), Huangi (*Hedysarum polybotrys*), or its extract, Dihuang (*Rehmannia glutinosa*), or its extract, Danggui (*Angelica sinensis*), Yuanzhi (*Polygala tenuifoila*), or its extract, Lingzhi (*Ganoderma* spp.), Fuling (*Poria cocos*), or its extract, Huperzine A, Lacithin, Metrifonate, Nocetile, folic acid, amino acids, creatine, fiber supplement, or any combination thereof.

This invention relates to two novel extracts: a combined extract and a crude saponin extract from Weguanguo husks and methods of their preparation. The extracts can be used to make medicines or health foods for preventing cerebral aging, improving cerebral functions and curing enuresis, frequent micturition, urinary incontinence, dementia, weak intelligence, and Alzheimer's disease, autism, brain trauma, Parkinson's disease and other diseases caused by cerebral dysfunction and treating arthritis, rheumatism, poor circulation, arteriosclerosis, Raynaud's syndrome.

Wenguanguo is a species of Sapindaceae family. Its scientific name is *Xanthoceras sorbifolia* Bunge. Wenguanguo is one common Chinese name, others are Wenguangguo Wenguanmu, Wenguanhua, Wenguanshu and Xilacedeng. This plant is a small tree up to 8 m in height. It features odd pinnately compound leaf, raceme with white flowers, capsules with thick and woody husks, and 1–8 black seeds. It is endemic to Northern China and has been cultivated in China for ages. The seed contains oil, up to 50% or more of which is edible. The stem and branches are Chinese herbs recorded in the Chinese materia medica specified in pharmacopoeia of The People's Republic China. The seeds have been used as a folk medicinal herb for curing enuresis for ages.

In recent years research showed the extracts from Wenguanguo seeds could yield potential remedies for treating cerebral diseases. A new medicine for curing enuresis has been developed from the kernel powders of Wenguanguo seeds.

This invention provides a novel extract from Wenguanguo husks and methods of their preparation. The combined extracts have improved medicinal properties compared with kernel powders and extracts from Wenguanguo seeds due to their higher saponin concentration (Table 1).

TABLE 1

Comparison of contents and components of extracts from husks and seeds

|   | Saponin | Saccharides | Protein | Water | Fat | Others |
|---|---------|-------------|---------|-------|-----|--------|
| A | 30–32   | 15–25       | 8–14    | 7–10  | 1–4 | —      |
| B | 10–19   | 20–30       | 15–20   | 10–15 | 1–10| —      |
| C | 2–4     | —           | —       | 55–65 | 7–16| 1–10   |

A: combined extracts from husks; B: extracts from seed kernel powder; C: seed kernel powders.

This invention provides a process of producing the combined extracts from the husks. The cost of producing the extracts from the husks is much lower due to the much lower cost of husks and a simple method for extraction. The price of husks is only 25% of that of the seeds.

The process of producing the extracts from seeds includes 10 steps: (1) collecting and drying the seeds; (2) removing shells from seeds to get the kernels; (3) pressing the kernels for pre-removing oils from the kernels to form the kernel bricks; (4) drying and milling the bricks to get the kernel powder; (5) removing the oils from the powder by alcohol extraction; (6) removing the alcohol from the powder; (7) drying and milling the powder again; (8) extracting the powder by ethanol to form ethanol extracts; (9) removing the ethanol to form the extracts; and (10) drying and sterilizing the extracts to form final products.

But the process of producing the husk extracts includes only 5 steps as follows:
1. collect and dry the husks;
2. mill said dried husks to form husk powder;
3. extract said husks powder with alcohol to form alcohol extracts;
4. remove the alcohol from said alcohol extracts to form aqueous extracts;
5. dry and sterilize said aqueous extracts to form the combined extracts.

Therefore, the cost of producing the combined extracts from husks with a concentration of 1 kg saponin is approximately is only 40% of the cost from seeds.

The combined extracts can be used in different forms, such as capsules and pills as the seed extracts do. However, the dosages of medicines made from the combined extracts are 3 capsules or pills/day compared with 18 capsules or pills/day from "Yiniaoting" due to the higher saponin concentration.

Therefore, it is much easier to be taken by patients, by children in particular, and also greatly reduces patients' costs.

This invention also provides a crude saponin extract from Wenguanguo husks (including fruit stems) and a process of their preparation. The crude saponin extracts is a further extract from the combined extracts, which is potentially a better remedy for preventing cerebral aging, improving cerebral function and curing enuresis, frequent micturition, urinary incontinence, dementia, weak intelligence and Alzheimer's disease, autism, brain trauma, Parkinson's disease and other diseases caused by cerebral dysfunctions and treating arthritis, rheumatism, poor circulation, arteriosclerosis, Raynaud's syndrome.

The main component in the extracts is saponin (over 50%). The process of producing the crude saponin extracts includes the following steps:
1. Extract the husk powder by alcohol or other organic solvent at a ratio of 1:2 4–5 times, 20–35 hours each time, to form alcohol extracts;
2. Collect and reflux said alcohol extracts 2–3 times at 80° C. to form second extracts;
3. Collect said second extracts and remove said alcohol from them to form combined extracts;
4. Resolve said combined extracts in water to form a aqueous solution;
5. Extract said solution by n-butanol to form a n-butanol extracts;
6. Chromatograph said n-butanol extracts to form the crude saponin extracts.

The crude saponin extracts can be used to make medicines or health foods in different forms for preventing cerebral aging, improving cerebral function and curing enuresis, frequent micturition, urinary incontinence, dementia, weak intelligence and Alzheimer's disease, autism, brain trauma, Parkinson's disease and other diseases caused by cerebral dysfunction and treating arthritis, rheumatism, poor circulation, arteriosclerosis, Raynaud's syndrome.

The two novel extracts provided by this invention are developed from a Chinese folk herb, Wenguanguo. They are the best remedy for curing enuresis without any side effects on the earth and could be a potential for preventing cerebral aging, improving cerebral function and curing enuresis, frequent micturition, urinary incontinence, dementia, weak intelligence and Alzheimer's disease, autism, brain trauma, Parkinson's disease and other diseases caused by cerebral dysfunction and treating arthritis, rheumatism, poor circulation, arteriosclerosis, Raynaud's syndrome.

The processes for preparing them are simple and low in cost.

This invention is further illustrated in the following examples.

EXAMPLE 1

A sample illustrating the method of producing a combined extract from husks.
1. Collect, dry and mill Wenguanguo husks to form 10 kg of husk powder;
2. Extract said husk powder by 20 L of ethanol 4–5 times, 20–35 hours each time;
3. Collect and reflux the ethanol extracts 2–3 times at 80° C. to form second extracts;
4. Collect said second extracts and remove ethanol from them to form aqueous extracts;
5. Dry and sterilize said aqueous extracts to form 140.5 g of combined extracts.

Components and contents of the extracts are as follows:

| Saponin | Saccharides | Protein | Water | Fat | Others |
|---------|-------------|---------|-------|-----|--------|
| 31.3    | 17.2        | 11.6    | 9.4   | 3.9 | 26.6   |

EXAMPLE 2

Fifty g of the combined extracts from Example 1 is softened with ethanol. The softened extracts are then sieved and granulated. The granulated extracts are capsulized to form 250 capsules. Ten capsules are packed in a bottle. The child's dosage for treating enuresis is one capsule, three times a day. One to three courses of treatment are needed and each lasts 15 days.

EXAMPLE 3

Fifty g of the combined extracts from Example 1 is softened with ethanol. The softened extracts are then sieved and powdered. The powder is mixed well with 450 g glucose, and then granulated. The granules are packed in small 2 g bags.

The dosage for treating child enuresis is 3 times/day, one bag each time. One to three courses of the treatment is needed, and each lasts 15 days.

EXAMPLE 4

Forty g of the combined extracts from Example 1 is softened with ethanol. The softened extracts are then sieved and powdered. The powders are mixed with 0.8 g starch, 0,4 g talcum powder and a little ethanol and then are pilled to form 200 pills. The pills can be used to treat enuresis and other disease caused by cerebral dysfunction. The dosage for treating child enuresis is 3 times per day, one pill each time. One to three courses of the treatment are needed, and each lasts 15 days.

EXAMPLE 5

The following is a sample illustrating the method of producing the crude saponin from husks.
1. Collect, dry and mill Wenguanguo husks to form 20 kg of husk powder;
2. Extract said husk powder using 40 L of ethanol 4–5 times, 20–35 hours each time;
3. Collect and reflux the ethanol extracts 2–3 times at 80° C. to form second extracts;
4. Collect said second extracts and remove ethanol from them to form aqueous extracts;
5. Dry said aqueous extracts to form 281.5 g of combined extracts;
6. Resolve said combined extracts in water to form an aqueous solution;
7. Extract said solution using n-butanol to form n-butanol extracts;
8. Fractionate said n-butanol extracts by droplet counter-current chromatography (d.c.c) using a $CHCl_3$—MeOH—$H_2O$ (35:65:40) solvent system (upper layer as the mobile phase, lower layer as the stationary phase).
9. Collect and combine said saponin fractions.
10. Remove the solvents by evaporation to yield 21.6 g of crude saponin.

EXAMPLE 6

9.0 g of the crude saponin from Example 5 mixed with starch, talcum powder and a little ethanol are pilled to form 250 pills. The pills are sterilized and packed for treating enuresis and other disease caused by cerebral dysfunctions.

The dosage for treating child enuresis is 3 times a day, one pill each time. One to three courses of the treatment are needed, and each lasts 15 days.

EXAMPLE 7

9.0 g of the crude saponin from Example 5 is encapsulated to form 250 capsules. Each of 30 capsules is packed in a bottle for treating enuresis and other disease caused by cerebral dysfunction. The dosage for treating child enuresis is 3 times for a day, one capsule each time. One to three courses of the treatment are needed, and each lasts 15 days.

REFERENCES

1. CN Pat. No. 1092992A, October 1994
2. CN Pat. No. 1092991A, October 1994
3. Chen Y et al., Chem. Pharm. Bull. 33(1): 127–134, 1985
4. Zhang TCH et al., Proceedings of national conference on medicinal plants, Dalian, China, 2000.
5. Zhu YCH et al., Platae medicinales Chinae boreali-orientalis, 710–711, Heilongjiang Science & Technology Publishing House, 1989.
6. Lu Guiyuan and Wang Yitao, Study of development of new Chinese medicines, 286–292, People Health Publish House, Beijing 1998.

What is claimed is:

1. An extract of Wenguanguo husk comprising at least 50% saponin by weight for use as a medicine or health food.

2. The extract of claim 1, comprising at least 75% saponin by weight.

3. The extract of claim 1, comprising at least 95% saponin by weight.

4. The extract of claim 1 wherein the extract comprises an aqueous extract.

5. The extract of claim 4 wherein the aqueous extract is formed from a high-temperature ethanol extract.

6. The extract of claim 1 wherein the extract is obtained from Wenguango husk powder.

7. An extract of wenguanguo husk, comprising at least 30% saponin by weight, saccharides at a range of about 15–25% by weight, protein at a range of about 5–14% by weight, water at a range of about 7–10% by weight, and fat at a range of about 1–4% by weight.

* * * * *